US006248532B1

(12) United States Patent
Keegan

(10) Patent No.: US 6,248,532 B1
(45) Date of Patent: *Jun. 19, 2001

(54) CREBA ISOFORM

(75) Inventor: Kathleen S. Keegan, Mercer Island, WA (US)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/407,715

(22) Filed: Sep. 28, 1999

Related U.S. Application Data

(60) Continuation of application No. 09/005,970, filed on Jan. 12, 1998, now Pat. No. 5,959,079, which is a division of application No. 08/721,684, filed on Sep. 27, 1996, now Pat. No. 5,854,016.

(51) Int. Cl.$^7$ .............................. C12Q 1/00; C12Q 1/02; C12Q 1/68; C12N 5/10; G01N 33/68
(52) U.S. Cl. .................. 435/6; 435/7.1; 435/29; 435/325; 435/375; 530/350
(58) Field of Search .................. 435/6, 7.1, 29, 435/91.1, 320.1, 325, 375, 455; 530/350

(56) References Cited

U.S. PATENT DOCUMENTS

| | | | |
|---|---|---|---|
| 5,476,926 | * 12/1995 | Spiegelman et al. | 536/24.1 |
| 5,641,486 | * 6/1997 | Hinrichs et al. | 424/139.1 |
| 5,656,452 | * 8/1997 | Rao et al. | 435/69.1 |
| 5,959,079 | * 9/1999 | Keegan | 530/350 |

OTHER PUBLICATIONS

Ahmed, "Significance of the Casein Kinase System in Cell Growth and Proliferation with Emphasis on Studies of the Androgenic Regulation of the Prostate," *Cell. Mol. Biol. Res.* 40:1–11 (1994).

Ausubel, "Immunoaffinity Chromatography," et al., *Current Protocols in Molecular Biology*, John Wiley & Sons (1993), pp. 10.11.8–10.11.22.

Bartel, et al., "Using the two–hybrid system to detect protein—protein interaction," *Cellular Interactions in Development: a Practical Approach*, Hartley (ed.), IRL Press; Oxford, pp. 153–179 (1993).

Chen and Okayama, "Calcium Phosphate–Mediated Gene Transfer: A Highly Efficient Transfection System for Stably Transforming Cells with Plasmid DNA," *Biotechniques* 6:632–638 (1988).

Chou and Blenis, "The 70 kDa S6 kinase: regulation of a kinase with multiple roles in mitogenic signalling," *Curr. Opin. Cell. Biol.* 7:806–814 (1995).

Digman, et al., "Accurate transcription initiation by RNA polymerase II in a soluble extract form isolated mammalian nuclei," *Nucl. Acids Res.* 11:1475–1489 (1983).

Durfee, et al., "The retinoblastoma protein associates with the protein phosphatase type 1 catalytic subunit," *Genes and Development* 7:555–569 (1993).

Hall and Peters, "Genetic Alterations of Cyclins, Cyclin–Dependent Kinases, and Cdk Inhibitors in Human Cancer," *Adv. Cancer Res.* 68:67–108 (1996).

Hollenberg, et al., "Identification of a New Family of Tissue–Specific Basic Helix–Loop–Helix Proteins with a Two–Hybrid System," *Mol. Cell. Biol.* 15:3813–3822 (1995).

Kapecchi, "Altering the Genome by Homologous Recombination," *Science* 244:1288–1292 (1989).

Marshall, "Opportunities for pharmacological intervention in the *ras* pathway," *Ann. Oncol.* 6:Suppl. 1:63–67 (1995).

Pollock and Treisman, "A sensitive method for the determination of protein–DNA binding specificities," *Nucleic Acids Res.* 18:6197–6204 (1990).

\* cited by examiner

*Primary Examiner*—John L. LeGuyader
*Assistant Examiner*—Thomas G. Larson
(74) *Attorney, Agent, or Firm*—Marshall, O'Toole, Gerstein, Murray & Borun

(57) ABSTRACT

The present invention relates generally to a novel CREBa polypeptide isoform, polynucleotides encoding the polypeptide, expression constructs comprising the polynucleotides, host cell transformed or transfected with the polynucleotides, methods for producing the polypeptide, and methods to identify inhibitors of binding between the CREBa and other polypeptides or polynucleotides.

13 Claims, No Drawings

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 3190 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 304..1866

(xi) SEQUENCE DESCRIPTION: SEQ ID NO: 1:

```
GGCACGAGGG ACTTTCTTGG GATGAGCGCT GCCTTTTTGG CTTCCTTTTG GATGCACAGC       60

CCGATTTAAC CCCTGCACCT TCCGCCCGAT CCCAGCAGGC TTGTCCTCCC CGGGGAGTCA      120

CAGATTTCCG AGGACAAGGG TCGCGTAGCC TTCGGCAGGG CTCTCCCGAG TTCCTGCTCC      180

AGTGCATAAG TTCCACGCGC GCACACGCCA AGTACACGGG GAGAAGCGTC TCACCGGCCC      240

GCGGCGGCTC TGCGCGGTCC CCTCCTGCCT CAGCATCCTC GGGCCTGCGC GGCGCCCACC      300

GCC ATG GAG GTG CTG GAG AGC GGG GAG CAG AGC GTC CTG CAG TGG GAC        348
    Met Glu Val Leu Glu Ser Gly Glu Gln Ser Val Leu Gln Trp Asp
     1               5                  10                  15

CGC AAG CTG AGC GAG CTG TCA GAG CCC GGA GAG ACT GAG GCC CTC ATG        396
Arg Lys Leu Ser Glu Leu Ser Glu Pro Gly Glu Thr Glu Ala Leu Met
             20                  25                  30

TAC CAC ACG CAC TTC TCG GAG CTC CTA GAC GAG TTT TCC CAG AAC GTC        444
Tyr His Thr His Phe Ser Glu Leu Leu Asp Glu Phe Ser Gln Asn Val
                 35                  40                  45

CTG GGT CAG CTC CTG AGT GAC CCT TTC CTC TCA GAG AAG AGC GAG TCA        492
Leu Gly Gln Leu Leu Ser Asp Pro Phe Leu Ser Glu Lys Ser Glu Ser
             50                  55                  60

ATG GAG GTG GAG CCA TCT CCA ACA TCA CCA GCG CCT CTC ATC CAG GCT        540
Met Glu Val Glu Pro Ser Pro Thr Ser Pro Ala Pro Leu Ile Gln Ala
65                  70                  75

GAA CAC AGC TAC TCT CTG AGC GAG GAG CCC CGG ACT CAG TCA CCA TTT        588
Glu His Ser Tyr Ser Leu Ser Glu Glu Pro Arg Thr Gln Ser Pro Phe
 80                  85                  90                  95

ACC CAT GCG GCT ACC AGC GAC AGC TTC AAT GAC GAG GAG GTG GAG AGT        636
Thr His Ala Ala Thr Ser Asp Ser Phe Asn Asp Glu Glu Val Glu Ser
                100                 105                 110

GAA AAA TGG TAC CTG TCT ACA GAG TTT CCT TCA GCT ACC ATC AAG AAA        684
Glu Lys Trp Tyr Leu Ser Thr Glu Phe Pro Ser Ala Thr Ile Lys Lys
            115                 120                 125

GAG CCA ATC ACA GAG GAG CAG CCC CCG GGA CTT GTC CCT TCT GTC ACT        732
Glu Pro Ile Thr Glu Glu Gln Pro Pro Gly Leu Val Pro Ser Val Thr
            130                 135                 140

CTG ACC ATC ACA GCC ATT TCC ACT CCT TTT GAA AAA GAA GAG TCC CCT        780
Leu Thr Ile Thr Ala Ile Ser Thr Pro Phe Glu Lys Glu Glu Ser Pro
145                 150                 155

CTG GAT ATG AAT GCT GGG GGG GAC TCC TCA TGC CAG ACG CTT ATT CCT        828
Leu Asp Met Asn Ala Gly Gly Asp Ser Ser Cys Gln Thr Leu Ile Pro
160                 165                 170                 175

AAG ATT AAG CTG GAG CCC CAC GAA GTG GAT CAG TTC TTA AAC TTC TCC        876
```

```
                                          -continued

Lys Ile Lys Leu Glu Pro His Glu Val Asp Gln Phe Leu Asn Phe Ser
            180                 185                 190

CCG AAA GAA GCC TCC GTG GAT CAA CTG CAC TTA CCA CCA ACA CCA CCC      924
Pro Lys Glu Ala Ser Val Asp Gln Leu His Leu Pro Pro Thr Pro Pro
            195                 200                 205

AGT AGT CAC AGC AGT GAC TCT GAG GGC AGC TTG AGC CCC AAC CCA CGC      972
Ser Ser His Ser Ser Asp Ser Glu Gly Ser Leu Ser Pro Asn Pro Arg
            210                 215                 220

CTG CAT CCC TTC AGC CTG TCT CAG GCC CAC AGC CCT GTC AGA GCC ATG     1020
Leu His Pro Phe Ser Leu Ser Gln Ala His Ser Pro Val Arg Ala Met
            225                 230                 235

CCC CGG GGC CCC TCT GCC TTG TCC ACA TCT CCT CTC CTC ACA GCT CCA     1068
Pro Arg Gly Pro Ser Ala Leu Ser Thr Ser Pro Leu Leu Thr Ala Pro
240                 245                 250                 255

CAT AAG CTG CAG GGA TCG GGC CCC CTG GTC CTG ACA GAA GAG GAG AAG     1116
His Lys Leu Gln Gly Ser Gly Pro Leu Val Leu Thr Glu Glu Glu Lys
                260                 265                 270

AGG ACC CTG GTT GCC GAG GGC TAT CCC ATT CCC ACC AAG CTG CCT CTG     1164
Arg Thr Leu Val Ala Glu Gly Tyr Pro Ile Pro Thr Lys Leu Pro Leu
                275                 280                 285

ACA AAA TCT GAG GAG AAG GCC CTG AAG AAA ATC CGG AGA AAG ATC AAG     1212
Thr Lys Ser Glu Glu Lys Ala Leu Lys Lys Ile Arg Arg Lys Ile Lys
                290                 295                 300

AAT AAG ATT TCT GCC CAA GAA AGC AGG AGA AAG AAG AAA GAA TAC ATG     1260
Asn Lys Ile Ser Ala Gln Glu Ser Arg Arg Lys Lys Lys Glu Tyr Met
305                 310                 315

GAC AGC CTG GAG AAA AAA GTG GAG TCT TGT TCA ACT GAG AAC TTG GAG     1308
Asp Ser Leu Glu Lys Lys Val Glu Ser Cys Ser Thr Glu Asn Leu Glu
320                 325                 330                 335

CTT CGG AAG AAG GTG GAG GTG CTG GAG AAC ACC AAT AGG ACT CTC CTT     1356
Leu Arg Lys Lys Val Glu Val Leu Glu Asn Thr Asn Arg Thr Leu Leu
                340                 345                 350

CAG CAA CTT CAG AAG CTT CAG ACT TTG GTG ATG GGG AAG GTC TCT CGA     1404
Gln Gln Leu Gln Lys Leu Gln Thr Leu Val Met Gly Lys Val Ser Arg
                355                 360                 365

ACC TGC AAG TTA GCT GGC ACA CAG ACT GGC ACC TGC CTC ATG GTC GTT     1452
Thr Cys Lys Leu Ala Gly Thr Gln Thr Gly Thr Cys Leu Met Val Val
                370                 375                 380

GTG CTT TGC TTT GCT GTT GCA TTT GGA AGC TTC TTT CAA GGC TAT GGG     1500
Val Leu Cys Phe Ala Val Ala Phe Gly Ser Phe Phe Gln Gly Tyr Gly
                385                 390                 395

CCT TAT CCT TCT GCC ACC AAG ATG GCT CTG CCC AGC CAG CAT CCT CTG     1548
Pro Tyr Pro Ser Ala Thr Lys Met Ala Leu Pro Ser Gln His Pro Leu
400                 405                 410                 415

TCA GAG CCA TAC ACA GCC TCC GTG GTG AGA TCC AGG AAC CTG CTA ATC     1596
Ser Glu Pro Tyr Thr Ala Ser Val Val Arg Ser Arg Asn Leu Leu Ile
                420                 425                 430

TAT GAG GAA CAC GCT CCC CTG GAA GAG TCG TCG AGC CCA GCC TCA ACC     1644
Tyr Glu Glu His Ala Pro Leu Glu Glu Ser Ser Ser Pro Ala Ser Thr
                435                 440                 445

GGG GAG CTG GGG GGC TGG GAC AGA GGC TCC TCT CTG CTC AGG GCA TCG     1692
Gly Glu Leu Gly Gly Trp Asp Arg Gly Ser Ser Leu Leu Arg Ala Ser
                450                 455                 460

TCG GGG CTT GAG GCC CTG CCA GAG GTG GAT CTT CCC CAT TTC CTT ATC     1740
Ser Gly Leu Glu Ala Leu Pro Glu Val Asp Leu Pro His Phe Leu Ile
                465                 470                 475

TCC AAT GAG ACG AGC TTG GAG AAG TCA GTA CTG TTG GAG CTT CAG CAG     1788
Ser Asn Glu Thr Ser Leu Glu Lys Ser Val Leu Leu Glu Leu Gln Gln
480                 485                 490                 495
```

```
CAC CTG GTC AGC AGC AAA CTG GAA GGG AAC GAA ACA CTC AAG GTT GTA    1836
His Leu Val Ser Ser Lys Leu Glu Gly Asn Glu Thr Leu Lys Val Val
                500                 505                 510

GAG CTG GAG AGG AGA GTG AAC GCC ACC TTC TGAGGAGAGC TCCACCCTCC       1886
Glu Leu Glu Arg Arg Val Asn Ala Thr Phe
                515                 520

TCTTCTCCTA ACTCCATCTG ATCGTCCTTT CAGTTTCCCC TTCACCACTG GATCTCGA    1946

AGGAGATGGC TAGTGTTACG GCTCGAGACA GGAGGCCAGC CCAGGGGGTT CTGCTTAT    2006

GTCCCCGTGG CTCTCCACAA AAGGGAGCTA GCACCTCTCC ATCCCTTTCT CTTACTGC    2066

TTGGAAATTA TTTTAGGGCT GAGATAGGGG TGGAACGAGC AGGCTTGTTT CCACCAAT    2126

TGCCAAGAAG ACACTGCCTG ATTCTTCCCC GGGAGGAGTG ACTCCTCTGA AGAAGACA    2186

ACTCATGTTC AGTTGAGACC CCAGACTCTA GCCACACACA TGCCACAGAC ATGCCAGG    2246

GTGGCAAAGC ACTGACTCCT GAGCTCCCTT CCTCACTAGG ACTCCAGTGT GACCCTGC    2306

TGAGAGGACC AAAGCGTCAT TGCAGTCTTC TCTCCACCCT GTACCCCGGA GTCCTGAT    2366

GATGTCTGCA GAGGCAGATG GGGCTCCCAC CATATTTTCA GGCCGCAAGT GCAATTCC    2426

AAGGCATCAG GCTCTTCTCT CCCAGGCTCT CCTGCCCACT GTGTTGTTTG TAGGACAC    2486

CCACACCCAC TCATACACAG CCTGCATCTC CACAGGACAA TAGCTCTGTC TCCCTGGC    2546

CCCCTCCCCA TTTGTAAATA GTATTTATTA GCTTGCTCAA GCTCCCAGCT GGCCATAG    2606

AAAAGATTTC CCCTTTCAAC CAGCAAAGTC TTCTGTTGGC CTTTGGAACA GGAGAGTC    2666

CGGAATCTAG GACCCTAGTC TTTGTACTTG ATGCCTTGTT TCCCCCCTTT TCTTCTTT    2726

AATTGGGGAC CTATAACATC ATCGCTGTTG CGGAATCCAC TTAGGCATGT GTCCCCTG    2786

GGATGAATAC ATGGGAATGG TGGATACTGT CTTCTGACTC AGGCTCTAGG CTCCATGG    2846

TCCTCTCTCT GGTCCTGCCA CACAGAAGGA AAGCCCTGTC CAGGATAATG AGCGTTGC    2906

ACACCCTTGC TAGCTTGTCC TGCCTACCTG CTTACCCCAC TCCCTCACCT TCCTCCTT    2966

CTTCTGCCCT CCATCCACCT GCCTTAACTA ATTGGGCTG GAGTTGGTCA TTTTTTGT     3026

ACCCACAGTG GTACCTTTTA CAGTCAGGTT TGGATACTTT GCAGCTCATC CAAAGAGA    3086

TAACTAAACC CTAAACTCTT TTTTTGTTGT TGTTGTTGTT GTTTTTTTTT TTTATGAT    3146

AAAAGTAAAA ATTGTAGTTT AAAAAAAAAA AAAAAAACT CGAG                    3190
```

(2) INFORMATION FOR SEQ ID NO: 2:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Val Leu Glu Ser Gly Glu Gln Ser Val Leu Gln Trp Asp Arg
 1               5                  10                  15

Lys Leu Ser Glu Leu Ser Glu Pro Gly Glu Thr Glu Ala Leu Met Tyr
            20                  25                  30

His Thr His Phe Ser Glu Leu Leu Asp Glu Phe Ser Gln Asn Val Leu
        35                  40                  45

Gly Gln Leu Leu Ser Asp Pro Phe Leu Ser Glu Lys Ser Glu Ser Met
    50                  55                  60

Glu Val Glu Pro Ser Pro Thr Ser Pro Ala Pro Leu Ile Gln Ala Glu
65                  70                  75                  80
```

-continued

```
His Ser Tyr Ser Leu Ser Glu Glu Pro Arg Thr Gln Ser Pro Phe Thr
                85                  90                  95

His Ala Ala Thr Ser Asp Ser Phe Asn Asp Glu Glu Val Glu Ser Glu
            100                 105                 110

Lys Trp Tyr Leu Ser Thr Glu Phe Pro Ser Ala Thr Ile Lys Lys Glu
            115                 120                 125

Pro Ile Thr Glu Glu Gln Pro Gly Leu Val Pro Ser Val Thr Leu
    130                 135                 140

Thr Ile Thr Ala Ile Ser Thr Pro Phe Glu Lys Glu Ser Pro Leu
145                 150                 155                 160

Asp Met Asn Ala Gly Gly Asp Ser Ser Cys Gln Thr Leu Ile Pro Lys
                165                 170                 175

Ile Lys Leu Glu Pro His Glu Val Asp Gln Phe Leu Asn Phe Ser Pro
            180                 185                 190

Lys Glu Ala Ser Val Asp Gln Leu His Leu Pro Pro Thr Pro Pro Ser
            195                 200                 205

Ser His Ser Ser Asp Ser Glu Gly Ser Leu Ser Pro Asn Pro Arg Leu
    210                 215                 220

His Pro Phe Ser Leu Ser Gln Ala His Ser Pro Val Arg Ala Met Pro
225                 230                 235                 240

Arg Gly Pro Ser Ala Leu Ser Thr Ser Pro Leu Leu Thr Ala Pro His
                245                 250                 255

Lys Leu Gln Gly Ser Gly Pro Leu Val Leu Thr Glu Glu Lys Arg
            260                 265                 270

Thr Leu Val Ala Glu Gly Tyr Pro Ile Pro Thr Lys Leu Pro Leu Thr
            275                 280                 285

Lys Ser Glu Glu Lys Ala Leu Lys Lys Ile Arg Arg Lys Ile Lys Asn
    290                 295                 300

Lys Ile Ser Ala Gln Glu Ser Arg Arg Lys Lys Lys Glu Tyr Met Asp
305                 310                 315                 320

Ser Leu Glu Lys Lys Val Glu Ser Cys Ser Thr Glu Asn Leu Glu Leu
                325                 330                 335

Arg Lys Lys Val Glu Val Leu Glu Asn Thr Asn Arg Thr Leu Leu Gln
            340                 345                 350

Gln Leu Gln Lys Leu Gln Thr Leu Val Met Gly Lys Val Ser Arg Thr
            355                 360                 365

Cys Lys Leu Ala Gly Thr Gln Thr Gly Thr Cys Leu Met Val Val Val
    370                 375                 380

Leu Cys Phe Ala Val Ala Phe Gly Ser Phe Phe Gln Gly Tyr Gly Pro
385                 390                 395                 400

Tyr Pro Ser Ala Thr Lys Met Ala Leu Pro Ser Gln His Pro Leu Ser
                405                 410                 415

Glu Pro Tyr Thr Ala Ser Val Val Arg Ser Arg Asn Leu Leu Ile Tyr
            420                 425                 430

Glu Glu His Ala Pro Leu Glu Glu Ser Ser Pro Ala Ser Thr Gly
            435                 440                 445

Glu Leu Gly Gly Trp Asp Arg Gly Ser Ser Leu Leu Arg Ala Ser Ser
    450                 455                 460

Gly Leu Glu Ala Leu Pro Glu Val Asp Leu Pro His Phe Leu Ile Ser
465                 470                 475                 480

Asn Glu Thr Ser Leu Glu Lys Ser Val Leu Leu Glu Leu Gln Gln His
                485                 490                 495

Leu Val Ser Ser Lys Leu Glu Gly Asn Glu Thr Leu Lys Val Val Glu
```

```
            500             505             510
Leu Glu Arg Arg Val Asn Ala Thr Phe
    515             520
```

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

```
CGCGGATCCT AATGGAGCTG AGAGTCGGG                              29
```

(2) INFORMATION FOR SEQ ID NO: 4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

```
CGCGGATCCG CTCATCGGTG CACGACAGA                              29
```

(2) INFORMATION FOR SEQ ID NO: 5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
CGGGATCCTC ACAGCTCCAC ATAAGCTGC                              29
```

(2) INFORMATION FOR SEQ ID NO: 6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

```
GGAATTCGCT CAAGGAGAGT CCTATTGG                               28
```

(2) INFORMATION FOR SEQ ID NO: 7:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
CAGGTCAGTT CAGCGGATCC TGTCGNNNNN NNNNNNNNNN NNNNNNNNNN NNNNNNNNNN   60
```

```
NNNNNNNNNN NNNNNNNNNN NNNNNNNNNN NNNNNNNNNN NNNNNNNNNN NNNNNNNNNN        120

NNNNNNNNNG AGGCGAATTC AGTGCAACTG CAGC                                    154
```

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

```
CAGGTCAGTT CAGCGGATCC TGTCG                                              25
```

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

```
GCTGCAGTTG CACTGAATTC GCCTC                                              25
```

(2) INFORMATION FOR SEQ ID NO: 10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

```
GAATCGGGCC GCCGAGATCT CATATGGAGC TGAGAGTC                                38
```

CREBA ISOFORM

This application is a continuation of U.S. patent application Ser. No.: 09/005,970, filed Jan. 12, 1998 which issued as U.S. Pat. No. : 5,959,079, which is a divisional of U.S. patent application Ser. No.: 08/721,684 filed Sep. 27, 1996, which issued as U.S. Pat. No. : 5,854,016.

FIELD OF THE INVENTION

The present invention relates to novel polynucleotides encoding polypeptides which bind to cAMP regulatory DNA sequences.

BACKGROUND OF THE INVENTION

Extracellular signal transduction leading to specific gene expression is often carried out by a series of enzymatic reactions which ultimately modulate activity of nuclear transcription factors. In one such example, extracellular signaling alters cytoplasmic levels of adenosine 3', 5'-monophosphate (cAP) which in turn modulates levels of active cAMP-dependent protein kinase (PKA). Once activated, PKA migrates into the nucleus and phosphorylates transcription factors which recognize DNA sequences common to genes that are regulated by cAMP signaling pathways. The common DNA sequence which permits cAMP regulation of gene expression has been designated the cAMP regulatory element (CRE) and the transcription factors which recognize and bind to the CRE are known as CRE-binding (CREB) proteins. It has been proposed that CREB proteins are ordinarily found in association with CRE DNA sequences and that the phosphorylation state of CREB determines the degree to which the protein is capable of inducing transcription of the associated gene. Once phosphorylated, CREB is able to bind a CREB-binding protein (CBP) which permits interaction of the complex with transcription factor TFIIB.

It is therefore apparent that regulation of the phosphorylation state of CREB is central to specific gene expression by cAM. The phosphorylation state of CREB, however, is not regulated solely by PKA. On the contrary, the degree of CREB phosphorylation is balanced between the activities of phophatases as well as kinases other than PKA. Thus, while CREB is a major participant in coordination of cAMP gene expression, CREB activity is subject to concurrent control by enzymes in other, non-cAMP related pathways.

Members in the CREB family of proteins contain conserved regions which carry out specific functions related to transcriptional activation. At the carboxy terminus, all CREB proteins have a leucine zipper region which permits dimerization of CREB with other CREB proteins or other heterologous transcription factor subunits. Adjacent the leucine zipper region, CREB proteins are characterized by a region designated the kinase inducible domain (KID) which is subject to phosphorylation by multiple kinases other than PKA, including for example, protein kinase C (PKC), casein kinase I (CKI) and casein kinase II (CKII), and possibly calcium-calmodulin dependent kinases I and II. At the amino terminus, CREB proteins each contain a DNA binding domain rich in basic amino acids. Despite seemingly subtle differences between proteins within the family, reports of variation in gene expression suggest that the proteins have unique physiological roles.

BRIEF SUMMARY OF THE INVENTION

In one respect the present invention provides purified and isolated polynucleotides (e.g., DNA sequences, RNA transcripts thereof and anti-sense oligonucleotides thereof) encoding a novel mouse cAMP regulatory element binding, designated mCREIBa, polypeptide well as polypeptide variants (including fragments and deletion, substitution, and addition analogs) thereof which display one or more DNA or protein binding activities, one or more specific gene transcription modulation activities, and/or immunological properties specific to mCREBa. DNA binding properties include recognition of specific DNA sequences through which mCREBa is able to modulate specific gene expression, while protein binding properties include interaction with various regulators of mCREBa activity, including any of a number of protein kinases, as well as interactions with specific and non-specific transcription factors. Preferred DNA sequences of the invention include genomic and cDNA sequences as well as wholly or partially chemically synthesized DNA sequences. A presently preferred olynucleotide is set out in SEQ ID NO: 1. Plasmid pBSmb3, comprising the preferred cDNA of the invention, in *E. coli* strain DH5αF' was deposited on September 18, 1996 with the American Type Culture Collection, 12301 Parklawn Drive, Rockville, Md. 20852, and assigned Accession Number 98171. Biological replicas (i.e., copies of isolated DNA sequences made in vivo or in vitro) of DNA sequences of the invention are contemplated. Also provided are autonomously replicating recombinant expression constructs such as plasmid and viral DNA vectors incorporating mCREBa sequences and especially vectors wherein DNA encoding mCREBa or a mCREBa variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells of the invention are conspicuously useful in methods for the large scale production of mCREBa and mCREBa variants wherein the cells are grown in a suitable culture medium and the desired polypeptide products are isolated from the cells or from the medium in which the cells are grown.

Novel mCREBa polypeptides of the invention may be obtained as isolates from natural cell sources, but, along with mCREBa variant products, are preferably produced by recombinant procedures involving host cells of the invention. A presently preferred amino acid sequence for a mCREBa polypeptide is set out in SEQ ID NO: 2. The recombinant products may be obtained in fully or partially phosphorylated or dephosphorylated forms, depending on the cell selected for recombinant expression and/or post-isolation processing. The mCREBa variants of the invention may comprise mCREBa fragments which include all or part of one or more of the domain regions having a biological or immunological property of mCREBa including, e.g., the ability to bind to a polypeptide or polynucleotide binding partner of mCREBa and/or inhibit binding of mCREBa to a natural binding partner. The mCREBa variants of the invention may also comprise polypeptide analogs wherein one or more of the specified amino acids is deleted or replaced: (1) without loss, and preferably with enhancement, of one or more biological activities or immunological characteristics specific for mCREBa; or (2) with specific disablement of a particular polypeptide/polypeptide or polypeptide/polynucleotide binding function. Analog polypeptides including additional amino acid (e.g., lysine or cysteine) residues that facilitate multimer formation are contemplated. Variant mCREBa polypeptides further include fusion polypeptides wherein all or part of mCREBa is expressed in conjunction with extraneous polypeptide sequences, including, but not limited to, for example poly-histidine tags, biotinylation tags, β-galactosidase chimera, or chimeric polypeptides including one or more the DNA binding or transactivating domains from various transcription factors.

Also comprehended by the present invention are antibody substances (e.g., monoclonal and polyclonal antibodies, antibody fragments, single chain antibodies, chimeric antibodies, CDR-grafted antibodies and the like) and other binding proteins (e.g., polypeptides and peptides) which are specific (i.e., non-reactive with previously identified CREBa isoforms to which mCREBa is structurally related) for mCREBa or mCREBa variants. Antibody substances can be developed using isolated natural or recombinant mCREBa or mCREBa variants. Binding proteins of the invention are additionally useful for characterization of DNA or polypeptide binding site structure(s) (e.g., epitopes and/or sensitivity of binding properties to modifications in mCREBa amino acid sequence).

Binding proteins are useful, in turn, in compositions for immunization as well as for purifying polypeptides of the invention and identifying cells which express the polypeptides on their surfaces. They are also manifestly useful in modulating (i.e., blocking, inhibiting or stimulating) DNA and/or polypeptide binding biological activities involving mCREBa, especially those mCREBa effector functions involved in specific and non-specific gene expression. Anti-idiotypic antibodies specific for anti-mCREBa antibody substances and uses of such anti-idiotypic antibody substances in modulating gene expression are also contemplated. Assays for the detection and quantification of mCREBa in body fluids, such as serum or cerebrospinal fluid, may involve, for example, a single antibody substance or multiple antibody substances in a "sandwich" assay format.

The scientific value of the information contributed through the disclosures of DNA and amino acid sequences of the present invention is manifest. As one series of examples, knowledge of the sequence of a cDNA for mCREBa makes possible the isolation by DNA/DNA hybridization of genomic DNA sequences encoding mCREBa and specifying mCREBa expression control regulatory sequences such as promoters, operators and the like. DNA/DNA hybridization procedures carried out with DNA sequences of the invention and under stringent conditions are likewise expected to allow the isolation of DNAs encoding allelic variants of mCREBa, other structurally related proteins sharing one or more of the biological and/or immunological properties specific to mCREBa, and proteins homologous to mCREBa from other species. DNAs of the invention are useful in DNA/RNA hybridization assays to detect the capacity of cells to express mCREBa. Also made available by the invention are anti-sense polynucleotides relevant to regulating expression of mCREBa by those cells which ordinarily express the same. As another series of examples, knowledge of the DNA and amino acid sequences of mCREBa makes possible the generation by recombinant means of mCREBa variants such as hybrid fusion proteins characterized by the presence of mCREBa protein sequences in association with various extraneous polypeptide sequences.

The DNA of the invention also permits identification of novel genes encoding binding partner polypeptides for mCREBa in any of a number of well known techniques, including for example, di-hybrid screening and gel overlay assays. The DNA and amino acid sequence information provided by the present invention also makes possible the systematic analysis of the structure and function of mCREBa and identification of those molecules with which it will interact. The idiotypes of anti-mCREBa monoclonal antibodies of the invention are representative of such molecules and may mimic natural binding proteins (peptides and polypeptides) through which mCREBa biological activities are modulated or by which mCREBa modulates intracellular events. Alternately, they may represent new classes of modulators of mCREBa activities. Anti-idiotypic antibodies, in turn, may represent new classes of biologically active mCREBa equivalents. In vitro assays for identifying antibodies or other compounds that modulate the activity of mCREBa may involve, for example, immobilizing mCREBa or a natural binding polypeptide or polynucleotide to which mCREBa binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of mCREBa binding.

In the alternative, DNA of the invention permits identification of inhibitors of mCREBa binding to other natural binding partners though utilization of a split hybrid assay, wherein mCREBa, or a protein binding domain fragment thereof, is expressed in a host cell as a fusion protein in combination with either a DNA binding or transactivating domain of one or more transcription factors. A natural binding partner of mCREBa is also expressed in the same host cell as a fusion protein in combination with either a DNA binding or transactivating domain of a transcription factor (whichever is not incorporated into the mCREBa fusion protein). Expression of the two fusion proteins, and subsequent association of the binding partners permits association of the DNA binding and transactivating domains forming an active transcription factor that leads to expression of a repressor protein. The expressed repressor protein, in turn, prevents expression of a reporter gene, thus significantly decreasing survival of the host cell. The thus transformed host cells can then be contacted with putative inhibitors of mCREBa/binding partner interaction and actual inhibitors identified as those which prevent mCREBa binding to its partner protein, thus preventing expression of the repressor protein which cannot therefore block expression of the reporter gene. An inhibitor therefore indirectly provides for a positive signal generated by expression and detection of the particular reporter gene product. There are at least three different types of libraries used for the identification of small molecule modulators. These include: (1) chemical libraries, (2) natural product libraries, and (3) combinatorial libraries comprised of random peptides, oligonucleotides or organic molecules. Chemical libraries consist of structural analogs of known compounds or compounds that are identified as inhibitory via natural product screening. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Combinatorial libraries are composed of large numbers of peptides, oligonucleotides, or organic compounds as a mixture. They are relatively easy to prepare by traditional automated synthesis methods, PCR cloning, or proprietary synthetic methods. Of particular interest are peptide and oligonucleotide combinatorial libraries. Still other libraries of interest include peptide, protein, peptidomimetic, multiparallel synthetic collection, recombinatorial, polypeptide libraries.

The DNA sequence information provided by the present invention also makes possible the development, by homologous recombination or "knockout" strategies [see, e.g., Kapecchi, *Science,* 244: 1288–1292 (1989)], of rodents or rabbits that fail to express a functional mCREBa protein or that express a variant mCREBa protein. Such rodents are useful as models for studying the activities of mCREBa and mCREBa modulators in vivo.

DETAILED SUMMARY OF THE INVENTION

The present invention is illustrated by way of the following examples. Example 1 describes isolation of a partial cDNA encoding a novel protein by virtue of its interaction with CK1b. Example 2 provides further characterization of the interaction between the novel protein and CKIδ. Example 3 relates to examination of tissue distribution of the novel mCREBa polypeptide. Example 4 addresses isolation of a full length cDNA encoding mCREBa. Example 5 describes generation of antibodies immunospecific for mCREBa. Example 6 relates to recombinant expression of mCREBa. Example 7 describes identification of the DNA binding site for mCREBa. Example 8 relates to generation of a high throughput screening assay for identification of modulators of mCREBa/DNA binding activity. Example 9 addresses use of mCREBa in a split hybrid assay to identify inhibitors of mCREBa/protein interactions.

Example 1

Isolation of cDNA Encoding A Protein That Interacts with CKIδ

In order to isolate cDNAs encoding proteins that interact with CKIδ, a two-hybrid screen was employed using an expression vector encoding a LexA-CKIδ fusion protein as bait. DNA encoding CKIδ was subcloned into the BamHI site of pBTM116 [Bartel, et al., in *Cellular Interactions in Development: a Practical Approach,* Hartley (ed.), IRL Press; Oxford, pp. 153–179 (1993)] by the following method. The coding region of CKIδHU was initially modified to incorporate BamHI restriction sites using PCR with primers EC 140 (SEQ ID NO: 3) and ECI41 (SEQ ID NO: 4) which produced a 1.3 kbp DNA fragment.

CGCGGATCCTAATGGAGCTGAGAGTCGGG SEQ ID NO: 3

CGCGGATCCGCTCATCGGTGCACGACAGA SEQ ID NO: 4

The amplification reaction included 300 ng CKIδHU template DNA, 1X PCR buffer (Perkin Elmer-Cetus), 1.5 mM MgCl$_2$, 200 uM each dATP, dCTP, dGTP, and dTTP, 10 ng/ml each primer ande 1 unit AmpliTaq (Perkin Elmer-Cetus). The reaction was carried out with an initial incubation at 94° C. for four minutes, followed by thirty cycles of incubation at 94° C for one minute, 50° C. for two minutes, and 72° C. for four minutes. The resulting PCR product was digested with BamHI and ligated into plasmid pAS1 [Durfee, el al., *Genes and Development* 7:555–569 (1993)] such that the encoded protein would be expressed containing an influenza hemagglutinin (HA) epitope tag. The resulting plasmid was transformed into *E. coil* by standard procedures and expression of the CKIδ fusion protein was confirmed by immunoblot using monoclonal antibody 12CA7 (Boehringer Mannheim) immunospecific for the HA epitope. The BamHI fragment encoding CKIδ was subsequently subcloned into the BamHI site of pBTM 116 to give plasmid pBTMCKIδ which was transformed into an *S. cerevisiae* strain L40 (MATa his3 Δ200 trp1-901 leu2-3,112 ade2 LYS2::( OexAop)$_4$ H1S3 L TRA3::(lexAop)$_8$,-lacZ GAL4) to generate strain CKIδ/L40. CKIδ40 was subjected to a large scale transformation with a cDNA library made from mouse embryos staged at days 9.5 and 10.5. The cDNA library was prepared in vector pVP16 according to the method of Hollenberg, et al. [*Mol. Cell. Biol.* 15:3813–3822 (1995)]. Approximately 40 million transformants were obtained as determined by survival on media lacking leucine and tryptophan.

Eighty-eight million transformants were assayed for protein/protein interaction by plating on selective media lacking leucine, tryptophan, and histidine. The ability of the yeast to grow in the absence of histidine suggested an interaction between CKIδ and a protein encoded by a library sequence. Colonies capable of growth on media lacking histidine were further screened by standard methods for the ability to express β-galactosidase encoded by a gene under transcriptional control of the LexA operator. One hundred of the yeast colonies that turned blue most rapidly were grown in liquid media lacking leucine and tryptophan and total yeast DNA was prepared by standard methods. The total yeast DNA was used to transform the *E. coli* strain C600, which lacks the ability to grow on media lacking leucine unless a plasmid expressing leucine is prese - ft. Bacteria were plated on agar containing carbenicillin (an ampicillin derivative) and lacking leucine. Individual colonies that grew under these conditions were grown up and plasmid DNA prepared.

Since many false positives can occur, positive plasmids were retested for interaction with the LexA-CKIδ fusion protein, as well as with a LexA-lamin fusion protein as a negative control. Briefly, the isolated cDNA library plasmid was cotransformed into L40 with either a plasmid encoding LexA-CKIδ or LexA-lamin, three yeast colonies from each transformation are picked and tested in a standard β-galactosidase blue/white assay. Cells that turned blue with LexA-CKIδ but not with LexA-lamin were grown up, the plasmid DNA isolated, and the sequence determined by standard methods. Search of the National Center for Biotechnology Information data base indicated three classes of cDNAs were obtained. Collectively, proteins encoded by the DNAs were designated CKIδ-delta-interacting proteins or DIPS.

One class of cDNAs, typified by a clone designated DIP25, contained a portion of a cDNA that was related, but not identical to Drosophila transcription factor dCREBa. The fill length clone was therefore designated mCREBa and contains two distinct amino acid motifs characteristic of CREB proteins. A region rich in basic amino acids, presumably a DNA binding region, is located at the amino terminus while a leucine zipper domain is found at the carboxyl terminus. A second class of DNAs was nearly identical to an EST clone T81950, while the third class showed no homology to any sequences in the databases.

Example 2

Characterization Of The Interaction Between the mCREBa DIP25 Clone and CKIδ

In order to further characterize the interaction between CKIδ and the mCREBa DIP25 fragment, the mouse clone was expressed in *E. coli* as a GST fusion protein as described below.

DIP25-encoding DNA was digested with BamHI and EcoRI and an approximately 500 bp fragment was isolated and ligated into plasmid pGEX3T (Pharmacia, city state) previously digested with BamHI and EcoRI. The resulting plasmid was transformed into E. coli. Protein expression was induced with addition of 0.2 mM IPTG to the media and a GST-DIP25 protein of approximately 45 kDa was expressed. The protein was purified by adsorption on glutathione agarose (Pharmacia) and used to assess the binding of DIP25 to CK1 6 in vitro as follows.

Recombinant CKIδ was produced as a histidine-tagged fusion protein in E.coli,[Ausubel, et al., Current Protocols in Molecular Biology, John Wiley & Sons (1993) pp. 10.11.8–10.11.22]. Briefly, CKIδ was cloned into the expression vector pET15b (Novagen). An NdeI restriction site was created at the 5'end of CKIδ by site directed mutagenesis and an NdeI/BamHI CKIδ fragment was ligated into pET15b previously digested with the same two enzymes. Site directed mutagenesis was carried out with an oligonucleotide designated KME18 (SEQ ID NO: 10) using the Mutagene Phagemid In Vitro Mutagenesis Kit, Version 2 (BioRad) according to manufacturer's suggested protocol.

GAATCGGGCCGCCGAGATCTCATATGGAGC
TGAGAGTC                                    SEQ ID NO: 10

The resulting plasmid was transformed into bacterial strain BL21DE3 and the cells grown to optical density ($A_{600}$) of 0.6. The cells were induced with 1 MM IPTG for 18 hours at 25° C., harvested, resuspended in break buffer (containing 20 mM $NaPO_4$, pH 8, 300 mM NaCl, 1 mM PMSF, 1 $\mu$M aprotein, 1 $\mu$M leupeptin) and lysed in a French Press. The lysate was centrifuged at 100,000 X g for 60 minutes and the supernatant loaded onto a Ni-NTA-Agarose column (QIAGEN, Germany). The column was washed with break buffer and protein eluted using a gradient of 0 to 200 mM imidazole. CKI activity associated with CKIδ eluted between 50 and 80 mM imidazole. The histidine-tagged fusion protein was incubated at 4° C. in binding buffer (50 mM NaCl, 10 mM Tris pH 7.5, 10% glycerol, 0.1% Triton) with the DIP25-GST fusion protein immobilized on glutathione agarose beads. After an hour incubation, the beads were washed three times in binding buffer and bound protein eluted by boiling in SDS sample buffer containing 2% SDS, 20 mM Tris, pH 6.8, 20% glycerol, and 0.001% bromphenol blue. A minor fraction of the DIP25-GST fusion protein bound the histidine- tagged CKIδ while no CKIδ bound to the negative control, immobilized GST alone. The inefficient binding may reflect either improper folding of the GST fusion protein or it may indicate a need for some post-translational modification of DIP25 that E. coli are unable to carry out.

Example 3

Tissue Distribution of mCREBa

In order to determine the tissue expression pattern of mCREBa mRNA, Northern blot analysis was carried out using containing a commercial membrane containing poly $A^+$RNA isolated from various mouse tissues and from whole mouse embryos at days 7, 11, 15, and 17 in gestation (Clontech, Palo Alto, Calif.). The membrane was probed following the manufacturer's suggested protocol using DNA generated by PCR from the mCREBa clone using the primers mCR-1 (SEQ ID NO: 5) and mCR-2 (SEQ ID NO: 6).

GGAATTCGCTCAAGGAGAGTCCTATTGG    (SEQ ID NO: 6)

CGGGATCCTCACAGCTCCACATAAGCTGC    (SEQ ID NO: 5)

The PCR included 50 ng DIP25 DNA as template, 1 X PCR buffer (Perkin-Elmer Cetus), 1.5 MM $MgCl_2$, 200 $\mu$M dATP, 200 $\mu$M dGTP, 200 $\mu$M dTTP, 1 $\mu$M dCTP, 50 $\mu$Ci $\alpha^{32}$P-dCTP, 10 ng/ml each primer, and 1 unit AmpliTaq (Perkin-Elmer Cetus). The reaction was carried out in a Perkin-Elmer Cetus Thermocycler Model 480 as follows: an initial denaturation cycle at 94° C. for four minutes, followed by 20 cycles of 94° C for 15 seconds, 60° C. for 15 seconds, and 72° C. for 30 seconds. Unincorporated nucleotides were removed using a Nuc-trap Push Column (Stratagene).

Two mRNAs were detected with one migrating at about 8 kb and the other at about 3.75 kb. The two mRNAs always detected together suggesting two splice variants. On the tissue RNA membrane, the highest levels of expression were seen in kidney, lung, and heart, with lower levels detected in skeletal muscle, liver, brain and testis. Very low expression was detected in spleen RNA on this particular blot. In the mouse embryo samples, expression of both the 8 kb and the 3.75 kb mnRNAs was highest at day 7 and lowest at day 11. After day 11, a progressive increase in expression was detected up to days 15 and 17.

In situ hybridization of mouse embryos was performed to determine which embryonic tissues expressed the mCREBa mRNA. Normal Balb/c mouse embryos were harvested and embedded in optimal temperature compound (Tissue Tech, Elkhart, Ind.) and whole embryos were sectioned at 6 micron thickness. Tissue sections were placed on Superfrost Plus® (VWR Scientific, Seattle, Wash.) and allowed to air dry overnight at room temperature. Sections not used immediately thereafter were stored at −70° C. After drying, sections were fixed in 4% paraformaldehyde (Sigma) in PBS for 20 minutes at room temperature, dehydrated using ethanol in increasing concentrations (70%, 95% and finally 100%) for one minute at 4° C. at each concentration, and air dried at room temperature. The sections were denatured for two minutes at 70° C. in a solution containing 70% formamide in 2X SSC. Sections were rinsed in 2X SSC at 4° C. and dehydrated and air dried again as previously described. Hybridization was carried out using $^{35}$S-labeled single stranded mRNA generated from murine DIP25 DNA by in vitro transcription using $^{35}$S-dUTP (Amersham). The labeled probe and diethylpyrocarbonate (DEPC)-treated water were added to a hybridization buffer of 50% formamide, 0.3 M NaCl, 20 mM Tris, pH 7.5, 10% dextran sulfate, 1 X Denhardt's, 100 mM dithiothreitol (DTT) and 5 mM EDTA. Prior to addition, the probe solution was heated for three minutes at 95° C. to denature the probe, and 20 $\mu$l of the buffer was applied to each tissue section which was then covered with a sterile RNAse free coverslip. Hybridization was carried out overnight at 50° C.

After hybridization, the sections were washed for one hour at room temperature in 4X SSC with 10 mM DTT, followed by additional washes for 40 minutes at 60° C. in a buffer containing 50% deionized formamide, 2X SSC, and 10 mM DTT and 30 minutes at room temperature in a 0.1 X SSC buffer. The sections were dehydrated and air dried as described above and dipped in Kodak (Rochester, N.Y.) NTB2 nuclear emulsion diluted 1:1 with 0.6 M ammonium acetate at 45° C. Slides were air dried 1 to 2 hours in the dark and exposed at 4° C. in the dark in the presence of a desiccant. After ten days exposure, the slides were developed in Kodak Dektol developer, washed with deionized water and submerged in Kodak fixer for four minutes at room temperature. The sections were then counterstained with hematoxylin and eosin (Sigma, St. Louis, Mo.). Results from this analysis are shown in Table 1.

TABLE 1

Expression of mCREBa mRNA in mouse embryos

|  | Day 15 | Day 16 | Day 17 | Day 18 |
|---|---|---|---|---|
| spinal roots | + | + | + | + |
| peripheral nerves | + | + | + | + |
| hindbrain | + |  |  |  |
| nasal areas | + | + |  |  |
| optic areas | + |  | + | + |
| unidentified region of the brain |  | + | + | + |
| tongue |  |  | + |  |
| bladder |  |  | + | + |
| kidney |  |  | + |  |
| lung |  |  | + |  |

Example 4

Isolation of a cDNA Encoding Full Length mCREBa

In order to obtain a full length cDNA encoding mCREBa, $5.4 \times 10^6$ clones from a mouse brain UniZAP XR cDNA library (Stratagene) were screened by hybridization with a probe generated by PCR from the mCREBa DIP25 clone using oligos mCR-1 and mCR-2 as described above. Hybridization was carried under conditions wherein nitrocellulose filters were incubated for 18 hours at 65° C. in 3X SSC, 5X Denhardt's, 0.1% sarkosyl, 20 mM $NaPO_4$, pH 6.8, 100 μg/ml single stranded salmon sperm DNA. One clone hybridized to the probe. The cDNA, designated pBSmb3, was isolated by in vivo excision according to the manufacturers suggested protocol and subjected to microsequencing. Sequencing analysis of the cDNA revealed a 3190 bp clone containing an open reading frame beginning at nucleotide 304 and ending at nucleotide 1866 with a predicted molecular weight of approximately 57 kDa. The nucleotide and amino acid sequences of the clone are set forth in SEQ ID NOs: 1 and 2, respectively. The DIP25 clone corresponds to nucleotides 1010 through 1514 of the full length mCREBa clone pBSmb3, encoding amino acids 237 through 405 representing both the basic DNA binding domain and the leucine zipper domain of the protein. Comparison of amino acids 406–508 of the leucine zipper region in dCREBa to amino acids 260 to 361 in the corresponding region of mCREBa reveals 78% identity and comparison of these regions at nucleotide level indicates 68% homology between nucleotides 2202 to 2511 of dCREBa and nucleotides 1081 to 1386 of mCREBa. In vitro transcription and translation of the clone using TNT kit (Promega, Madison, Wis.) produced a protein product that migrated slightly slower than the predicted molecular weight (about 75 kDa), possibly caused by the highly charged basic DNA binding domain or the secondary structure formed in the leucine zipper domain. In addition, a sub clone of pBSmb3 was generated by digesting the plasmid with EcoRI and XhoI to produce a 1.8 kb fragment that was ligateded into pBluescript sk⁻ previously digested with the same two enzymes. The resulting plasmid was designated pBSmb3E/X. In vitro transcription and translation of the encoded gene resulting in production of a polypeptide of approximately 75 kD suggesting that the entire coding sequences for the protein was contained on the 1.8 kb fragment. Further, amino acid sequence analysis suggests that, similar to other CREB isoforms, mCREBa may potentially be phosphorylated by kinases other than CKIδ, including but not limited to other CKI isoforms, CKII, cdc2, MAP kinase, and S6 kinase.

Example 5

Production and Characterization of mCREBa Antibodies

Polyclonal antibodies specific for mCREBa were generated using the DIP25-GST expression product of plasmid pGEX3T-DIP25 described above. Briefly, C600 bacteria transformed with the plasmid were grown to an absorbance at 600 nm of 1.8, at which point expression of DIP25-GST was induced for five hours by addition of 0.1 mM IPTG which acted on the endogenous lac promoter. Following induction, bacteria were harvested by centrifugation and resuspended in phosphate buffered saline (PBS) containing 1 mM pbenylmethylsulfonylfluoride (PMSF), 1μg/ml leupeptide, and 1 μg/ml pepstatin. The cells were lysed in a French press and centrifuged for twenty minutes at 12,000 x g. The supernatant was incubated for one hour with 3 ml of a 50% slurry of glutathione-Sepharose 4B (Pharmacia), after which the resin was pelleted and washed three times in PBS. Protein was eluted from the resin using 50 mM glutathione in 10 mM Tris, pH 8.0.

Female New Zealand White rabbits were initially immunized with 200 μg DIP25-GST antigen mixed with Freund's complete adjuvant injected subcutaneously at multiple sites. Subsequent boosters were carried out with protein that was first boiled in SDS sample buffer, loaded onto an SDS polyacrylamide gel, and electroeluted from gel slices. Booster antigen preparation was mixed with Fruend's incomplete adjuvant and administered at approximately 21 day intervals following the first immunization. Test bleeds taken after immunizations 3, 4, and 5.

The immunization resulted in two polyclonal antisera designated 6179 and 6144. In order to determine if the antisera recognized mCREBa, pBSmb3 was transcribed and translated in vitro in the presence of $^{35}$S-methionine using a TNT kit (Promega). The translation extract was diluted to 0.5 ml with NP40 IBP (containing 1% Nonidet P40, 50 mM Tris, pH 7.5, 100 mM NaCl, 1 mM EDTA) and incubated on ice for one hour with 5 μl rabbit antisera. Following incubation, 20 μl of a 50% slurry of protein A agarose (Repligen) was added and incubation continued on ice for an additional 20 minutes. Immune complexes were collected by centrifugation and washed three times in NP40 IPB. Protein was eluted from the complexes by boiling in SDS sample buffer and loaded onto an SDS polyacrylamide gel. After separation, the gel was fixed in acetic acid and methanol, treated with the fluor Amplify (Amersham), dried, and exposed to x-ray film. Autoradiography indicated that both antisera reacted with the 79 kDa expression product from pBSmb3E/X described above.

In order to determine whether the antisera reacted with mCREB expressed in mammalian cells, an expression plasnid encoding a mammalian CREB was constructed as follows. Parental plasmid pcDNA 3 (Invitrogen) was digested with restriction enzymes EcoRI and XhoI and ligated with the 1.8 kbp EcoRI/XhoI fragment from pBS rmb3E/X described above and encoding the complete mCREB protein. The resulting plasmid was used to transiently transform a human embryonic kidney cell line 293T by the method of Chen and Okayama [*Biotechniques* 6:632–638 (1988)]. Cell lysates were generated 48 hours after transformation in buffer containing 1% Trito ,. X-100, 10 MM Tris, pH 7.6,5 mM EDTA, 50 mM NaCl, 30 mM $Na_4P_2O_7$, 50 mM NaF, 100 μM $Na_3VO_4$, 1 mM PMSF, 1 μg/ml aprotein, and 1 μg/ml leupeptin and the lysate centrifuged at 10,000 x g. One hundred pg cleared lysate was loaded onto a 10% SDS polyacrylamide gel and immunoblots were produced by standard techniques. Both antisera, diluted 1:1000, reacted with a protein of approximately 79 kDa protein in the in lysate from cells transfected with pcDNA3 containing the mCREB sequences.

Example 6

Expression of Recombinant mCREBa

Recombinant mCREBa was expressed in E. coli as a fusion with a protein using a modified Pinpoint expression vector (Promega) which permits expression of a biotinylated protein when the host cells are grown in the presence of biotin. Briefly, a 1.8 kb NcoI/XhoI fragment was excised from pBSmb3 and subcloned into expression plasmid araBC previously digested with NcoI and XhoI. The resulting intermediate plasmid contained mCREBa-encoding sequences under the control of the arabinose promoter. In order to fuse a biotin tag to mCREB, an EcoRI/NcoI promoter fragment from the expression plasmid arabio1b was inserted into the intermediate plasmid such that the mCREBa coding sequence was in frame with a biotin tag and under the control of the arabinose promoter. The resulting plasmid was designated arabiomCREB. Bacteria were transformed with arabiomCREB by standard techniques and grown to mid-log phase in Luria Broth containing 2 $\mu$M biotin. Expression of biotin-mCREBa was induced with 1% arabinose, the bacteria harvested by centrifugation, and the pellet was resuspended in 50 mM Tris. pH 8.0, 100 mM NaCl, 1 mM EDTA, 5 mM EGTA, and 1 mM DTT. The cells were lysed in a French Press, insoluble material removed by centrifugation, and the supernatant was adjusted to 150 mM NaCl, 5% glycerol, 0.1% Tween 20,4 mM DTT. The biotinylated mCREBa was purified by addition of streptavidin-agarose (Promega) and incubation for 4 hours at 4° C. with rocking. Bound protein was washed three times with buffer containing 50 mM Tris, pH8.0, 100 mM NaCl, 1 mM EDTA, 5 mM EGTA, and 1 mM DTT. Glycerol was added to a final concentration of 10% and the biotin-mCREBa protein bound to streptavidin-agarose stored at −70° C.

Example 7

Determination of the DNA Binding Site of mCREBa

The binding specificity of mCREBa for DNA sequences is determined using Binding Site Selection as described by Pollock and Treisman [*Nucleic Acids Res.* 18:6197–6204 (1990)] which permits rapid identification of the DNA binding site of a protein from random oligonucleotides. To perform Binding Site Selection of the mCREBa site, the biotin-mCREBa protein prepared as described above is incubated with a 26 nucleotide random oligomer flanked by specific nucleotides that will anneal to oligonucleotide primers in a PCR reaction.
Random olionucleotide SEQ ID NO: 7

5'CAGGTCAGTTCAGCGGATCCTGTCG-(A/G/C
/T)$_{26}$GAGGCGAATTCAGTGCAACTGCAGC-3'

The binding reaction is carried out under conditions of low ionic strength to avoid interrupting salt-sensitive binding reactions. Binding buffer containing Dignam's buffer D [Digman, et al., *Nucl. Acids Res.* 11: 1475–1489 (1983)] with protease inhibitors, 0.1% Nonidet P-40, 1 mg/ml acetylated bovine serum albumin (Promega), is combined with 200 ng Poly (dIdC)-Poly (dIdC) (Pharmacia), 1 pg biotin-mCREBa, and 0.4 ng random oligonucleotide and incubation carried out for thirty minutes on ice to permit protein/DNA complex formation. Streptavidin agarose is added to the binding reaction and following incubation overnight at 4° C. with rocking, mCREBa/DNA complexes formed are collected by centrifugation. Complexes are washed two times with the above binding buffer and DNA eluted from complex by incubation at 45° C. in buffer containing 200 $\mu$l 5 mM EDTA, 0.5% SDS, 100 mM sodium acetate, 50 mM Tris, pH 8.0. DNA is phenol extracted, mixed with 10 $\mu$g of rabbit muscle glycogen (Boehringer Mannheim) as carrier, and ethanol precipitated. Recovery of DNA is quantitated by Cerenkov counting.

The recovered DNA is amplified in a 10 pl PCR reaction including 150 $\mu$g each of primers F and R (SEQ ID NOs: 8 and 9, respectively), 5 $\mu$Ci $^{32}$p -dCTP, 20 $\mu$M dCTP, 50$\mu$each dATP, dGTP, dTTP, 1 mg/ml bovine serum albumin, 1X PCR buffer (Perkin-Elmer Cetus), 1.5 mM MgCl$_2$, and 1 unit AmpliTaq (Perkin-Elmer Cetus).

Primer F                                          SEQ ID NO:8
        5'-CAGGTCAGTTCAGCGGATCCTGTCG-3'

Primer R                                          SEQ ID NO:9
        5'-GCTGCAGTTGCACTGAATTCGCCTC-3'

Amplification is carried out with an initial denaturation incubation at 94° C. for four minutes followed by 15 cycles of 94° C. for one minute, 62° C. for one minute, and 72° C. for one minutes. The product of this PCR reaction is gel purified by after electrophoresis on a 8% nondenaturing polyacrylamide gel and used (instead of the random oligonucleotide) for reselection of DNA binding sequences as described above. This may be repeated 3 or 4 times. The DNA final products are digested with BamHI and EcoRI which flank the defined DNA binding site and cloned into the BamHI and EcoRIsites in the polylinker region of the vector pGL2-promoter (Promega). Plasmid p GL2promoter is a vector that expresses firefly luciferase under control of the SV40 early promoter with a polylinker region upstream from the promoter that permits insertion of potential regulatory sequences. The resulting plasmids are subjected to DNA sequence analysis to determine a consensus nucleotide sequence of the DNA binding site for mCREBa.

DNA binding of mCREBa to the defined sequence is confirmed using a gel mobility shift assay. Briefly, purified biotin-mCREBa is incubated for 15 minutes at 2 1° C. with a 0.1 pmol/$\mu$l $^{32}$P-labelled oligonucleotide containing a DNA binding site identified as described above in buffer containing 50 mM Tris, pH8, 50 mM NaCl, 50 $\mu$M DTT, 1 mM EDTA, 10% glycerol, 5 mM MgCl$_2$, 5 mM spermidine, 0.05% Nonidet P-40, 3 pg bovine serum albumin, and 1 $\mu$g poly(dIdC)-poly(dIdC) (Pharmacia). After appropriate incubation, the binding mixture is loaded onto a 4% non-denaturing polyacryla ride gel and mCREBa binding to a radiolabelled DNA sequence determined by a higher molecular weight shift of the DNA as compared to control DNA in the absence of mCREBa protein.

As further characterization of mCREBa binding to previously identified DNA sequences, pGL2 constructs containing the mCREBa DNA binding site is cotransfected into 293T cells with pcDNA3-mCREBa and the ability of expressed mCREBa to either activate or repress transcription of the reporter construct is determined. Cells are transfected by the method of Chen and Okyama [supra], harvested after 48 hours and assayed for luciferase activity using a Luciferase Assay Kit (Promega) according to manufacturer's suggested protocol.

Example 8

High Throughput Screen for Modulators of mCREBa DNA Binding Activity

An assay for high throughput screening of small molecule inhibitors (combinatorial libraries, natural product libraries, and/or chemical libraries) is established based on the defined DNA binding site of mCREBa determined above. A filter binding assay is designed in which the ability of recombinant mCREBa to bind to a $^{32}$P-labeled DNA sequence is monitored by quantitating radioactivity bound to protein immobilized on nitrocellulose filter. The $^{32}$P-labeled DNA is designed to be sufficiently small in order that it will not bind to nitrocellulose in the absence of previously immobilized the mCREBa protein. Putative modulators are incubated with the immobilized protein and modulators of DNA binding activity are identified as those which effect an increase or decrease in the ability of the DNA to bind to the protein.

An alternative assay is established in which recombinant biotinylated mCREBa is bound to streptavidin-coated plates (Pierce), incubated with candidate small molecule modulators and the $^{32}$P-labeled DNA sequence added. Modulators are defined as those molecules that increase or decrease binding of mCREBa to the labeled DNA sequence.

Secondary assays involve treating cells transfected with pGL2-promoter/DNA binding site constructs with defined modulators followed by assay of activity of the product of the reporter gene.

Example 9

Identification of Modulators of mCREBa Binding to Other Proteins

Co-pending U.S. patent application Ser. No. 08/721, 684 (Attorney Docket Number 27866/33487, filed concurrently herewith) describes in detail a "split hybrid assay" technique to identify molecules which disrupt specific protein/protein interaction. The specification of that application is incorporated herein by reference.

In order to isolate cDNAs which encode proteins that interact with CKIδ, the two hybrid assay was performed using a LexA-CKIδ fusion protein as bait. The coding region of CKIδ was sub dloned into a BamHI site of pBTM116 and transformed into a yeast strain designated CKIδb/L40 (MAT a his3 Δ200 trp1-901 leu2-3 112 ade2 LYS::(lexAop)$_4$HlS3 URA3::(lexAop)$_8$,-1cZ GAL 4). CKIδ/L40 was subjected to a large scale transformation with a cDNA library made from mouse embryos staged at days 9.5 and 10.5. Approximately 40 million transformants were obtained. Eighty-eight million were plated onto selective media lacking leucine, tryptophan and histidine. The ability of yeast transformants to grow in the absence of histidine suggested that there was an interaction between CKIδ and some library protein.

In a second screening, interaction of the two proteins was assayed by the ability of the interaction to activate transcription of β-galactosidase. Colonies that turned blue in the presence of X-gal were streaked onto media lacking leucine, tryptophan and histidine, grown up in liquid culture and pooled for isolation of total DNA. Isolated DNA was used to transform E. coli strain 600 which lacks the ability to grow on media lacking leucine. Colonies that grew were used for plasmid preparation and three classes of cDNA were identified. One class was closely related to a Drosophila transcription factor dCREBa.

When CKIδ/CREB interaction was examined in the split hybrid assay, cells were shown to grow on media containing histidine, but in the absence of histidine, growth was inhibited. Addition of small amounts of tetracycline to the cell culture restored the cell's ability to grow, suggesting that the interaction between CKIδ and CREBa was very weak.

In order to identify molecules capable of disrupting binding interaction between mCREBa and CKIδHU, the split hybrid assay is employed in the presence of putative inhibitors selected from, for example, chemical libraries, natural product libraries, and combinatorial libraries. Similarly, inhibitors of interaction between mCREBa and other interacting kinases, as well as other proteins, are also identified in the same techniques. Expression plasmids for other mCREBa-interacting proteins are constructed using techniques similar to those used in construction of a CKIHU expression plasmid. The split hybrid assay is then performed in the presence of various putative binding inhibitors wherein inhibition is determined by the ability of the host cell to grow on media lacking a nutritional requirement.

In the split hybrid assay, mCREBa, or a protein binding domain fragment thereof, is expressed in a host cell as a fission protein in combination with either a DNA binding or transactivating domain of one or more transcription factors. Examples of mCREBa binding partners include cdc2 [see review in Hall and Peters, *Adv. Cancer Res.* 68:67–108 (1996)], CKI and CKII isoforms [see review in Ahmed, *Cell Mol. Biol. Res.* 40:1–11 (1994)], MAP kinase [see review in Marshall, *Ann. Oncol* 6: Suppl. 1:63–67 (1995)], and S6 kinase [see review in Chou and Blenis, *Curr. Opin. Cell. BioL* 7:806–814 (1995)]. A natural binding partner of mCREBa is also expressed in the same host cell as a fusion protein in combination with either a DNA binding or transactivating domain of a transcription factor (whichever is not incorporated into the mCREBa fusion protein). Expression of the two fusion proteins, and subsequent association of the binding partners permits association of the DNA binding and transactivating domains forming an active transcription factor that leads to expression of a repressor protein. The expressed repressor protein, in turn, prevents expression of a reporter gene, thus significantly decreasing survival of the host cell. The thus transformed host cells can then be contacted with putative inhibitors of mCREBa/binding partner interaction an d . actual inhibitors identified as those which prevent mCREBa binding to its partner protein, thus preventing expression of the prepressor protein which cannot therefore block expression of the reporter gene. An inhibitor therefore indirectly provides for a positive signal generated by expression and detection of the particular reporter gene product. Sources of potential inhibitors amenable to this type of assay can be found in chemical compound libraries, libraries of natural products isolated from microorganisms, animals, plants, and/or marine organisms, multiparallel synthetic collections, and/or combinatorial, recombinatorial, peptidomimetic, peptide, polypeptide or protein libraries.

What is claimed is:

1. A method to identify modulators of mCREBa binding to DNA comprising the steps of:
    a) incubating mCREBa with a DNA sequence known to specifically bind mCREBa;
    b) determining the degree of binding between mCREBa and the DNA sequence;
    c) repeating step (a) in the presence of a putative modulator of mCREBa binding to the DNA sequences; and
    d) comparing binding of mCREBa with the DNA sequence in the presence of the putative modulator in step (c) to the degree of binding determined in step (b), and identifying the putative modulator as an enhancer when increased binding is detected in the presence of the putative modulator and identifying the putative modulator as a repressor when decreased binding in the presence of the putative modulator is detected.

2. A method to identify an inhibitor of binding between mCREBa or binding fragment thereof and a mCREBa-binding protein or binding fragment thereof comprising the steps of:
    a) producing host cells transformed or transfected with DNA comprising:
    a repressor gene encoding a repressor protein, said repressor gene under transcriptional control of a promoter;
    a selectable marker gene encoding a selectable marker protein; said selectable marker gene under transcriptional control of an operator; said operator regulated by interaction with said repressor protein;
    a first recombinant fusion protein gene encoding mCREBa or a binding fragment thereof in frame with either a DNA binding domain of a transcriptional activating protein or a transactivating domain of a transcriptional activating protein; and
    a second recombinant fusion protein gene encoding a mCREBa-binding protein or binding fragment thereof in frame with either a DNA binding domain of a transcriptional activating protein or a transactivating domain of a transcriptional activating protein, whichever domain is not encoded by the first fusion protein gene, said second binding protein or binding fragment thereof capable of interacting with said first binding protein or binding fragment thereof such that interaction of said second binding protein or binding fragment thereof and said first binding protein or binding fragment thereof brings into proximity a DNA binding domain and a transactivating domain forming a functional transcriptional activating protein; said functional transcriptional activating protein acting on said promoter to increase expression of said repressor gene.

b) growing the host cells in the absence of a test compound and under conditions which permit expression of said mCREBa or binding fragment thereof and said mCREBa-binding protein or binding fragment thereof such that said mCREBa or fragment thereof and said mCREBa binding protein or binding fragment thereof interact bringing into proximity said DNA binding domain and said transactivating domain forming said functional transcriptional activating protein; said transcriptional activating protein acting on said promoter to increase expression of said repressor protein; said repressor protein interacting with said operator such that said selectable marker protein is not expressed;

c) confirming lack of expression of said selectable marker protein in said host cell;

d) growing said host cells in the presence of a test compound;

e) determining expression of said selectable marker protein in the presence of said test compound, and f) comparing expression of said selectable marker protein in the presence and absence of said test compound wherein increased expression of said selectable marker protein is indicative that the test compound is an inhibitor of binding between said first binding protein or binding fragment thereof and said second binding protein or binding fragment thereof.

3. The method of claim 2 wherein said DNA binding domain and said transactivating domain are derived from a common transcriptional activating protein.

4. The method of claim 2 wherein one or more of the repressor gene, the selectable marker gene, the first recombinant fusion protein gene, and the second recombinant fusion protein gene are encoded on distinct DNA expression constructs.

5. The method of claim 2 wherein said selectable marker protein is an enzyme in a pathway for synthesis of a nutritional requirement for said host cell such that expression of said selectable marker protein is required for growth of said host cell on media lacking said nutritional requirement.

6. The method of claim 2 wherein said host cell is a yeast cell or a mammalian.

7. The method of claim 3 wherein said selectable marker gene encodes HIS3.

8. The method of claim 3 wherein said repressor protein gene encodes a tetracycline resistance protein.

9. The method of claim 3 wherein said operator is a tet operator.

10. The method of claim 3 wherein said promoter is selected from the group consisting of the LexA promoter, the alcohol dehydrogenase promoter, the Gal4 promoter.

11. The method of claim 3 wherein said DNA binding domain derived from a protein selected from the group consisting of LexA and Gal4.

12. The method of claim 3 wherein said transactivating domain is derived from a protein selected from the group consisting of VP16 and Gal4.

13. The method of claim 3 wherein the mCREBa-binding protein is selected from the group consisting of CKI, CKII, cdc2, MAP kinase, and S6 kinase.

* * * * *